July 22, 1969 M. J. MURRAY Plant Pat. 2,908
MINT STRAIN
Filed Sept. 15, 1967
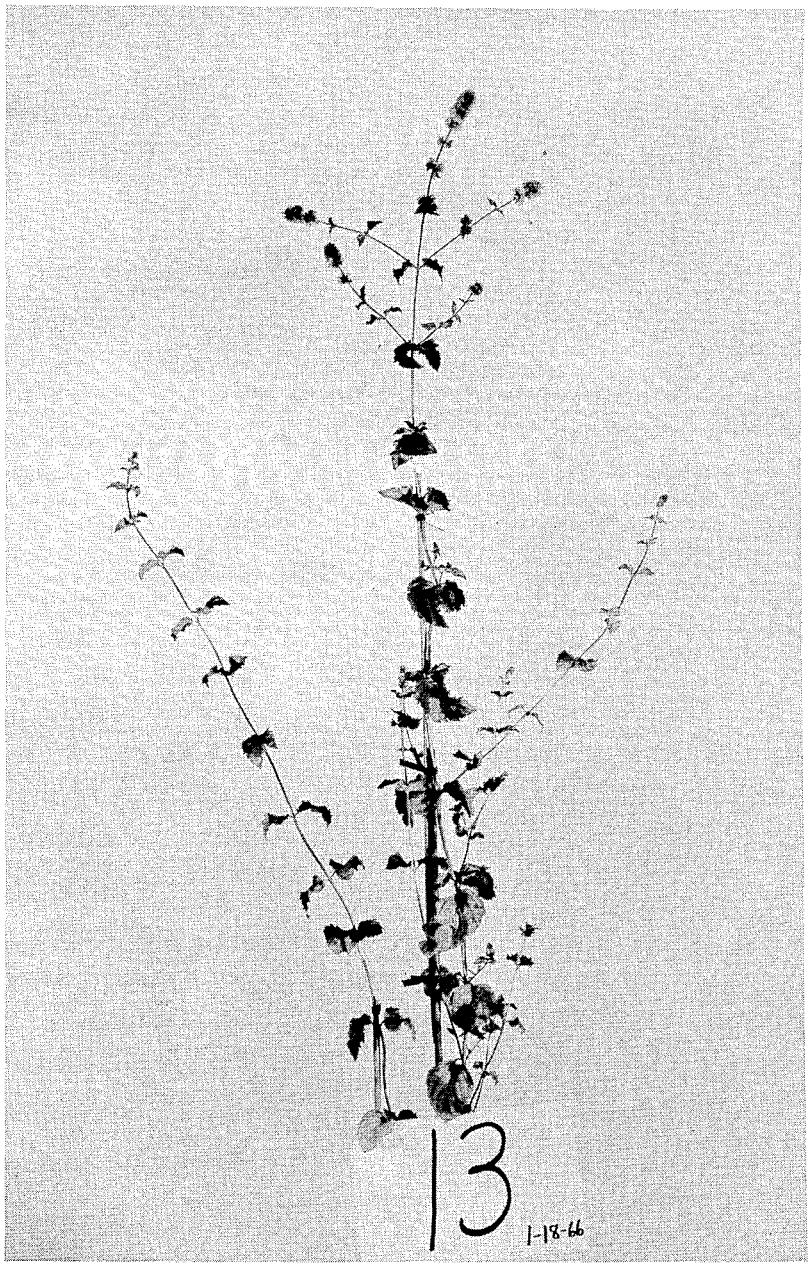

United States Patent Office

Plant Pat. 2,908
Patented July 22, 1969

2,908
MINT STRAIN

Merritt J. Murray, Kalamazoo, Mich., assignor to A. M. Todd Company, Kalamazoo, Mich., a corporation of Michigan Filed Sept. 15, 1967, Ser. No. 668,260
Int. Cl. A01h 5/00
U.S. Cl. Plt.—89 1 Claim

ABSTRACT OF THE DISCLOSURE

A new and distinct variety of mint plant substantially as herein shown and described, being an adapted, high-yielding strain having excellent stolons which are winter hardy, characterized particularly by its distinctive, fresh, clean, herbaceous, warm, hay-lavender odor with a suggestion of sage and bergamont-like notes and its pleasant and balsamic but not minty dry out; its very high degree of wilt resistance to the pathogen *Verticillium albo-atrum* R. and B. var. *menthae* Nelson, especially when compared with its *Mentha citrata* seed parent; its hardy characteristics under climatic conditions favorable to the growth of mint plants as represented by *Mentha piperita* L., especially in the Oregon area of mint production; and its production of an oil which has as its principal components linalyl acetate and linalool as compared with the oil of its male parent which has as its principal components menthone and pulegone.

This invention relates to a new and distinct variety of mint plant which was orginally produced by hybridizing a clonal strain (European origin unknown) of diploid *Mentha citrata* Ehrh. as a seed parent to a pollen parent which was a highly Verticillium wilt-resistant selection known as 59–198. The male parent, 59–198, was a specific wilt-resistant selection from a sib cross of two highly wilt-resistant $S_1$ inbreds (or once self-pollinated first generation inbreds) of *Mentha crispa* L. (also taxonomically known as *Mentha spicata* L. var. *crispata*).

Drawings

In the drawing, which is a photographic illustration of the new variety, the figure is a view of the plant showing the general form of the stems, leaves, and flowers.

Seed parent

In the above cross, the Mueller strain of *Mentha citrata* had to be the seed parent since it is male sterile.

Male parent

The male parent used in the cross was known in our laboratory as 59–198 when it was hybridized, but it was actually derived from a sib cross made in 1950 and the seedlings grown in 1951 as Culture 51–1226. The selected seedling from Culture 51–1226 known as number 1 had no rust, no Verticillium wilt symptoms, and a weak menthone odor. It had very slightly hairy stems, a very erect habit, and early maturity (medium maturity for *M. crispa* lines, but early maturing in comparison to seed parent and hybrids) with small crisp leaves. This selection should have had and did have high wilt-resistance since it came from the cross of two selected first generation $S_1$ inbreds of *M. crispa* which had been selected for their superior wilt-resistance in 1948. To recapitulate the history of the $S_1$ inbreds, we self-pollinated a clonal strain of *Mentha crispa* L. in the summer of 1947 and planted the selfed seeds in the spring of 1948 as Cultures 48–202 and 48–201. We selected two seedlings as being very superior in Verticillium wilt-resistance and these were very thoroughly tested in 1949 and designated as 202–3 and 201–9. As we have noted previously, these two first generation inbreds were hybridized, or sib-crossed, in the summer of 1950 to give Culture 51–1226 from which we selected the single seedling that was used as a male parent and known in our laboratory as 59–198. The disease resistance and vigor of this wilt-resistant selection (59–198) were confirmed through subsequent field tests made during the nine-year period between its initial selection in 1951 and its utilization in 1961 in the hybridization to *Mentha citrata*.

As one can note, the Plot 13 strain was derived from the interspecific hybridization of two species, *Mentha citrata* Ehrh. and *Mentha crispa* L. The Mueller strain of *Mentha citrata* was utilized in this program and its European origin is unknown to us. *Mentha crispa* was a clonal strain from the original A. M. Todd collection of species from European sources made a considerable number of years ago and its exact geographical origin is unknown.

History and first vegetative propagation

The hybridization of the Mueller strain of *Mentha citrata* and 59–198 was accomplished in the summer of 1961. About seven hundred seeds were planted in the spring of 1962 as Culture 62–1006. We transplanted 677 seedlings and 325 of these from this specific cross were grown on the Mueller farm as numbers 4830 to 4981 and 6710 to 6882. Of these 325 seedlings, 233 were discarded at harvest time, whereas 92 were assigned the harvest numbers 1412 to 1469 and 1889 to 1922. The single plant harvested as 62–1440 gave on distillation 4.95 grams of oil which was odor evaluated and assayed by vapor chromatography.

This strain was first vegetatively propagated in April 1963 to give a six-foot plot numbered 63–245. Its oil quality, yield and disease resistance were studied in this 1963 six-foot plot and subsequently in a $\frac{1}{100}$ acre plot in 1964, known as Plot 64–104. This strain was further tested in 1965 and 1966 in a $\frac{1}{20}$ acre plot known as 1965 Plot 13. The wilt-resistance test of the Plot 13 strain was conducted in Indiana during the summers of 1965, 1966, and 1967.

General objectives of this breeding program

The specific cross giving rise to Plot 13 was made for the following reasons. We utilized the Mueller strain of *Mentha citrata*, since it is our tallest strain of *Mentha citrata*. We chose 59–198 as the male parent since we wished to hybridize to a very highly wilt-resistant male parent so that our resulting hybrids might have a considerable degree of wilt-resistance. This was deemed important since all our stock strains of *Mentha citrata* are extremely susceptible to Verticillium wilt. Any hybrid to be usable must also be better adapted to the climatic conditions of the U.S. mint-growing areas than our native European stock strains of *Mentha citrata* appear to be. A suitable hybrid must also have excellent stolons and overwinter better than any of the natural strains of *Mentha citrata* which we have tested.

Distinctive characteristics of Plot 13

While one could say that this Plot 13 strain is intermediate in appearance between the parental strains, it is readily distinguishable from either of the parents in the following ways.

Differences between *Mentha citrata* and Plot 13

*Height.*—The Plot 13 strain is about the same height as the seed parent but is taller than the male parent. On the alluvial soil of the Oregon production area the seed parent, *Mentha citrata*, is 17–20" tall while the Plot 13 strain is 21–24" tall in the first year growth and 17–24" tall in the second year growth. On the organic soils of northern Indiana, the Plot 13 hybrid is 18–21" tall. Under greenhouse conditions, the seed parent is 58–72" tall, whereas the Plot 13 strain is 63–72" tall.

*Plant habit.*—*Mentha citrata* is an erect bush type with few branches rising mostly in the upper half of the plant and having an open habit with large, nearly flat leaves. The Plot 13 strain is an erect, short-appearing, bush type very much branched from the base with fine stems and small leaves and having a compact growth with dense foliage. The seed parent strain of *Mentha citrata* is not as spreading nor as reclining as other *Mentha citrata* strains. Since the seed parent is slender, it appears tall in comparison to Plot 13 which is very spreading although there are no essential differences in height measurements.

*Maturity.*—The Plot 13 hybrid has medium maturity, with the first-year crop in full bloom on September 1st and the second-year crop 90% past blooming on September 1st, whereas the seed parent has very late maturity with very few flower spikes in bloom on September 1st.

*Yield.*—The oil yield of the Plot 13 hybrid is double that of the *Mentha citrata* parent and under optimum conditions should exceed 100 pounds per acre, whereas the seed parent strain usually yields 30–40 pounds per acre and at best 50 pounds per acre.

*Stems.*—The seed parent strain of *Mentha citrata* has coarse, large stems which are brittle and tend to split rather than lop or recline. The hybrid has medium-sized, sturdy, erect, very much branched stems which are not brittle and generally remain erect at maturity.

*Degree of stem branching.*—The seed parent has relatively few secondary branches and almost no tertiary branches, whereas the Plot 13 hybrid is much more freely branched with numerous secondary and tertiary branches.

*Stem size.*—The stem diameter of the seed parent is usually 4–5 mm., while the stems of the hybrid are usually 2½–3 mm. in diameter in both the first- and second-year plants in the Oregon area and also in the muck-grown plants of northern Indiana.

*Leaf shape.*—Strains of *Mentha citrata* frequently have oval to ovate leaves but the seed parent strain used in our breeding program has ovate leaves. The Plot 13 hybrid typically has ovate leaves which are frequently narrowly ovate, but the uppermost leaves do approach an ovate-lanceolate shape since they taper to the apex. Leaf shape is not a prime distinguishing characterstic between the seed parent and the Plot 13 hybrid.

*Leaf size.*—The lower main stem leaves of field plants of the Plot 13 hybrid measure ⅞–1½" long x ½–1" wide, but the leaves of greenhouse and muck-grown plants are larger and frequently 2–2½" long x 1½–2" wide. The main stem leaves of greenhouse plants of the seed parent are usually 2⅞" long x 1 1/16" wide and are generally slightly larger than the leaves of the Plot 13 strain.

*Leaf petiole.*—The leaf petioles of greenhouse-grown plants of the seed parent are usually 15–20 mm. long, whereas those of the Plot 13 strain are usually 7–10 mm. long in the greenhouse, 3–5 mm. long in Idaho- and Oregon-grown plants, and 5–7 mm. long in muck-grown Indiana plants.

*Leaf apex.*—While some *Mentha citrata* strains have rounded or very obtuse leaf apexes, the seed parent strain has an acute leaf apex and is similar to the Plot 13 hybrid except that the hybrid's uppermost smaller leaves are sometimes very sharply tipped.

*Leaf base.*—The seed parent usually has an acute leaf base, whereas the lower leaves of the hybrid are usually sub-cordate and the uppermost leaves are usually tapered to an acute junction with the leaf petiole. Some of the largest lower main stem leaves of field-grown plants of the hybrid, and the larger leaves of greenhouse-grown plants, are occasionally cordate.

*Leaf margin.*—While some strains of *Mentha citrata* have very inconspicuous teeth on the leaf margin, the seed parent strain of *Mentha citrata* has regular, serrate, very conspicuous teeth. In contrast, the Plot 13 hybrid has irregular, large, very prominent teeth which are finger-like on a sub-lacerate margin. The uppermost leaves of the hybrid are usually less lacerate and frequently have serrate, sharp teeth.

*Leaf teeth.*—The main stem leaves of greenhouse-grown plants of the seed parent usually have 12–13 regular teeth on one side of the leaf margin with the teeth measuring 1½ mm. on the acute side, whereas comparable leaves of the Plot 13 hybrid usually have 4–8 irregular teeth on one side of the leaf margin, most often 6 teeth, which measure 3–4 mm. and are sometimes as large as 4–5 mm. The leaves of field plants of the Plot 13 strain are particularly distinctive from the seed parent since the lower main stem leaves are crisp and have finger-like teeth, or fimbria, which measure 2–3 mm. in length. The upper leaves of the hybrid are less crisp with less lacerate margins and have more nearly serrate teeth which are 1–2 mm. long. All leaves of the seed parent usually have very regular serrate teeth which are definitely not finger-like, whereas leaves of the hybrid strain have irregular teeth which vary in size, shape and number but are definitely finger-like on the most crisp lower leaves.

*Leaf texture.*—While certain strains of *Mentha citrata* have definitely coriaceous, or leathery, leaf texture, the seed parent and the Plot 13 strain are alike in having a normal non-coriaceous leaf texture.

*Leaf color.*—The leaves of the hybrid strain are normal green in color except that the leaf petioles and major leaf veins may develop some red anthocyanin color but this is usually less than that found in the seed parent which has fully anthocyanin development on the leaf petioles, major leaf veins and is sometimes extreme enough to give the leaves a bronzed appearance. This characteristic is somewhat variable since the anthocyanin color requires sunlight for development.

*Leaf contour.*—In the seed parent strain of *Mentha citrata,* the leaf tip of mature leaves curls or rolls downward often making a half circle, whereas the mature and even secondary leaves of the Plot 13 hybrid are half-crisp and tend to make a half twist rather than turn downward from the tip. The upper leaves of the hybrid and especially the leaves of greenhouse-grown plants are usually less crisp and less twisted.

*Leaf surface.*—The leaves of the seed parent are flat with prominent veins and with considerable wrinkling upward between the major leaf veins, especially in greenhouse-grown plants, whereas the leaves of the hybrid are semi-crisp and wrinkled with very considerable bulging upward between the major leaf veins.

*Flower spikes.*—The flower spikes of the seed parent are typically capitate, or dome-shaped, as in *Mentha aquatica* L., whereas the Plot 13 strain hybrid has a broadly cylindrical flower spike of medium size which is of somewhat smaller diameter than the flower spikes of of *M. citrata.* The flower spike of the hybrid is more peppermint-like in appearance, rather than being similar to *Mentha aquatica* L. or *Mentha citrata* which are typically capitate or globose.

*Flower spike size.*—The capitate heads of the seed parent are ½–¾" long x ½–¾" wide with the dome-shaped heads usually as wide as long, whereas the terminal flower spikes of the hybrid are usually 1–1½" long while the flower spikes of the secondary branches are smaller and usually not more than ¾" long. The capitate heads of the seed parent are in metric measurements 13–20 mm. long x 13–20 mm. wide, about as wide as long, whereas the end portion of the terminal spikes of the hybrid are usually 25–32 mm. long x 11–12 mm. in diameter in pressed flowering specimens. The fruiting spikes are usually 25–40 mm. long x 7–9 mm. in diameter and are generally shorter in second-year Oregon-grown plants or in midwestern-grown plants on organic soil. Flowering and fruiting spikes of greenhouse-grown plants are frequently broader and the fruiting spikes are often 14–17 mm. in diameter.

*Corolla color.*—Both the seed parent and the Plot 13 hybrid have a medium lavender flower color.

*Flower spikes subtended by.*—While many strains of *M. citrata* have bracts that are half to full-sized leaves, the seed parent has bracts that are leaf-like with serrate margins but 1/10 to 1/4 the size of normal leaves. The Plot 13 strain has bracts that are about the same size as the seed parent, but the brackets of the hybrid have very large, fimbriate teeth.

*Extent of flowering.*—The seed parent produces small flower heads sparingly by September 1st, whereas the Plot 13 hybrid produces a profusion of flower spikes which are in full bloom on September 1st in first-year plants. Second-year plants have a profusion of small flower heads which are 90% past flowering on September 1st.

*Stolons.*—The stolons of the seed parent are long and slender in greenhouse plants but they are often short and poorly developed in field plantings in the western mint growing area. In contrast, the hybrid Plot 13 strain produces excellent peppermint-like stolons.

*Stolon survival.*—Under western field conditions, the production of stolons by the seed parent is erratic and uncertain, with survival over winter very uncertain from very short stolons or from the old crowns. In contrast, the hybrid has excellent stolons which from all present evidence overwinter well even under unfavorable climatic or weather conditions.

*Oil compositions.*—On the basis of a three-year average, the seed parent has 58% linalyl acetate, 30% linalool and 12% other components, whereas the hybrid has 58% linalyl acetate, 29% linalool and 13% other oil components. While there is no essential difference between the seed parent and the Plot 13 hybrid in the two major oil components, the minor oil constituents of a terpene hydrocarbon nature are not presumed or known to be identical.

*Odor.*—The seed parent has a typical *Mentha citrata* odor whereas the Plot 13 strain has a fresh, clean, herbaceous, warm, hay-lavender odor with suggestions of sage and bergamot-like notes to make a good topnote and an excellent dry-out, pleasant and balsamic but not minty.

*Stem color.*—The Plot 13 strain has a medium amount of anthocyanin color on the stem and exposed stolons, whereas the seed parent usually has very red anthocyanin color on the stems and exposed stolons. As pointed out previously, under some environmental conditions, the leaf petioles of the seed parent may be very reddish and the leaves may have a reddish, or bronze effect, whereas this extreme color developmnet is not usually found in the Plot 13 strain.

*Plant pubescence.*—The seed parent and the Plot 13 hybrid are alike in appearing glabrous to the unassisted eye, but at 20× magnification both have a few short, stubby hairs ½–1 mm. long especially on the leaf petioles and the veins of the lower leaf surface. The hybrid generally has fewer hairs than the seed parent, although the hairs are similar in appearance. This is not a very distinctive difference.

*Calyx pubescence.*—The seed parent has a few ¼–½ mm. long hairs on the lobes and veins of the calyx, and the Plot 13 strain is similar to the seed parent in these characteristics, but usually has more hairs on the margins of the calyx lobes.

*Corolla pubescence.*—The seed parent and the Plot 13 strain are alike in having a few inconspicuous hairs on the outer lip of the corolla.

*Flower pedicels.*—The seed parent and the Plot 13 strain are essentially alike in having 1–2 mm. long pedicels which are essentially glabrous but occasionally do have a few very short hairs.

*Size differences of flower parts.*—No consistent essential differences were noted in the size of the flower parts despite the differences in chromosome numbers and origin.

*Number of flowers in a flower cluster.*—Both the seed parent and the Plot 13 hybrid have 15 flowers usually in each flower cluster.

*Resistance to Verticillium wilt.*—The seed parent as well as all other natural strains of *M. citrata* so far tested in our laboratory are extremely susceptible to the pathogen *Verticillium albo-atrum* R. and B. var. *menthae* Nelson, whereas the Plot 13 strain was our most resistant hybrid strain in our 1966 wilt test on very wilt-infested organic soil in northern Indiana. This test plot was so thoroughly infested with wilt spores that peppermint, *Mentha piperita* L., and other susceptible mints were 90–100% infected and wilted.

*Fertility.*—The seed parent is male sterile with rudimentary anthers but is seed fertile, whereas the Plot 13 strain is usually male sterile with rudimentary anthers and highly seed sterile when pollinated by other fertile species.

*Diploid chromosome number.*—*Mentha citrata* Ehrh. has been reported as having 96 chromosomes. *Mentha crispa* L. from which the male parent was derived has been reported as having 48–51 chromosomes. The Plot 13 hybrid strain presumably has about 72 chromosomes since it was derived from crossing the above two fertile species.

Comparison of the male parent to the Plot 13 hybrid strain

From an overall viewpoint, the male parent (59–198) closely resembles *Mentha crispa* L. (also known as *Mentha spicata* L. var. *crispata*) from which it was derived, whereas the Plot 13 hybrid resembles the first generation hybrids obtained from hybridizing *M. citrata* Ehrh. or *Mentha aquatica* L. to *M. spicata* L. or *M. crispa* L. Since the fertile species *M. aquatica* L. and *M. citrata* Ehrh. are reported as having 96 chromosomes and the fertile species *M. spicata* L. and *M. crispa* L. as having 48–51 chromosomes, one may presume logically that the $F_1$ hybrids have about 72 chromosomes. Under proper environmental conditions, the male parent is perfectly fertile, whereas the Plot 13 strain is usually male sterile like the seed parent but unlike the seed parent (which is seed fertile) is highly seed sterile.

The male parent is 11–13″ tall and shorter than the Plot 13 strain which is 17–24″ tall. The male parent is very early maturing with most of the flowers gone by September 1st, whereas comparable first-year plants of the hybrid are usually in full bloom on September 1. Although second-year plants tend to flower somewhat earlier than first-year plants, the male parent is always somewhat earlier maturing than the Plot 13 strain. The Plot 13 strain has a growth habit similar to the male parent but the fine, wiry, stiff, erect, slender, much-branched stems of the male parent are usually 2–2½ mm. in diameter and smaller than those of the hybrid which has medium-sized stems 2½–3 mm. in diameter.

The ovate to ovate-lanceolate leaves of the male parent are similar to those of the hybrid but the leaves of the male parent are nearly sessile with very short petioles, usually 2 mm. or less, whereas the hybrid has longer petioles which are 3–7 mm. long. The lower mainstem very crisp leaves of the male parent usually have more typically cordate leaf bases, often are almost as broad as long, with extremely lacerate margins and typically larger, 3–5 mm. long, fimbria. In contrast, the lower mainstem semi-crisp leaves of the Plot 13 hybrid have mostly rounded or subcordate leaf bases, have less lacerate margins and the fimbria of the semi-crisp leaves are typically smaller and 2–3 mm. long (occasionally 3–5 mm.). The very crisp leaves of the male parent are also more extreme than the semi-crisp leaves of the Plot 13 hybrid in having more pronounced upward bulging of the leaf surface betwen the major veins and in being more twisted or curled.

The fruiting heads of the male parent are generally

20–40 mm. long x 6–7 mm. wide and thus are more slender than those of the Plot 13 hybrid, generally 25–40 mm. long x 7–9 mm. in diameter. Of minor interest, the bracts subtending the flower spikes of the male parent are leaf-like but are usually smaller than those of the Plot 13 strain.

The stolons of the male parent are very fibrous and overwinter well even under extreme climatic conditions, and the Plot 13 variety resembles the male parent in these characteristics.

The male parent has a menthone-pulegone odor, since menthone and pulegone are the principal oil components in this strain, whereas there are only trace amounts (if any) of linalyl acetate and linalool, the principal oil components of the Plot 13 hybrid strain.

Of minor importance, the male parent appears nearly glabrous to the unassisted eye, although there are a few long hairs on the stems, bracts to the flower clusters, and the lower leaf surface, especially on the midrib. These hairs are usually longer than those found in the Plot 13 strain and they appear most prominently on the flower pedicel, calyx lobes, leaf midrib, and a few occur on the outer lip of the corolla as in the Plot 13 hybrid.

The male parent and the Plot 13 strain are alike in being highly resistant to the pathogen, *Verticillium albo-atrum* R. and B. var. *menthae* Nelson.

Comparison of the Plot 13 hybrid strain and the Plot 4 hybrid strain

In comparison to Plot 13, the Plot 4 strain is somewhat later in maturity (medium plus versus medium), is taller (since mostly 23–26" tall versus 21–24" tall for Plot 13) with a more spreading and open habit with coarser, less branched stems bearing larger flat leaves which are in direct contrast to the smaller semi-crisp and twisted leaves with lacerate margins characteristic of Plot 13. The large mainstem leaves of the Plot 4 strain project essentially flat and do not wrinkle upward between the major leaf veins and the leaves have regular, serrate, conspicuous teeth 1–1½ mm. long and are very unlike the semi-crisp, twisted and wrinkled mainstem leaves of the Plot 13 strain, which have 2–5 mm. long fimbria. The 8–13 mm. long leaf petioles of the Plot 4 strain are longer than those of the Plot 13 strain (usually 3–7 mm.).

The flower clusters of the Plot 13 strain are less crowded in the flower spike as compared to the denser more compact flower spikes of Plot 4 and the flower spikes of the Plot 4 strain are usually broader and often larger than those of the Plot 13 strain.

The oil of the Plot 13 strain has less linalyl acetate and more lonalool than the oil of the Plot 4 strain.

Of less conspicuous nature, the Plot 4 strain has fewer hairs on the stems and leaves than the Plot 13 strain but the hairs on the calyx are longer (½–1 mm.) than those of Plot 13 (½ mm. or less). While Plot 13 has inconspicuous hairs on the outer lip of the corolla, no hairs of this type are generally found on the lip of the corolla in the Plot 4 strain.

The Plot 4 strain has only slight wilt-resistance while the Plot 13 strain is highly wilt-resistant.

General summation

In comparison to the seed parent strain of *Mentha citrata*, this variety (Plot 13) is more freely branched near the base and has a more compact growth habit and denser foliage. It is earlier in maturity, higher yielding, having less coarse, less brittle, and much more freely branched stems, and having ovate main stem leaves which are similar in shape and size but which are semi-crisp leaved with lacerate, incised margins and fimbriate teeth like the male parent instead of the nearly flat leaves of the seed parent which have regular serrate conspicuous teeth. The leaves of this variety are less crisp with less pronounced lacerate margins than those of the male parent, but the leaf petioles are longer than those of the male parent whose leaves are nearly sessile, or with very short petioles which are 2 mm. or less long. In contrast, the new variety has shorter petioles (3–7 mm.) than the seed parent (15–20 mm.) The ovate leaves of the seed parent are flat, sometimes rolling at the tip, but have regular, serrate, conspicuous teeth 1.5 mm. long and usually 12–13 teeth on the side of a leaf margin, whereas the Plot 13 hybrid has semi-crisp leaves with lacerate and incised margins and fimbriate irregular-sized teeth which are 2–5 mm. long with 4–8 teeth on one side of the leaf margin. This variety has terminal flowers, only slightly sub-axillary, and the flower spikes are usually subtended by small-sized leaves, but the terminal spikes are usually 1–1½ inches long and cylindrical and peppermint-like in contrast to the dome-shaped capitate or globose heads of the seed parent which are likewise typical of the species *M. citrata* Ehrh. and *Mentha aquatica* L. This variety has, on the average, 58% linalyl acetate and 29% linalool, but is particularly noted for its herbaceous, warm, hay-lavender odor with suggestions of sage and bergamot. This variety is particularly of interest because of its winter hardiness, its adaptation to the mint-growing areas of Oregon and neighboring states, and its excellent wilt-resistance to the serious pathogen *Verticillium albo-atrum* R. and B. var. *menthae Nelson*. Unlike the seed parent, this variety is seed sterile, whereas the seed parent is seed fertile. Both are usually male sterile. The male parent is wholly fertile.

I claim:

1. A new and distinct variety of mint plant substantially as herein shown and described, being an adapted, high-yielding strain having excellent stolons which are winter hardy, characterized particularly by its distinctive fresh, clean, herbaceous, warm, hay-lavender odor with a suggestion of sage and bergamot-like notes and its pleasant and balsamic but not minty dry out; its very high degree of wilt-resistance to the pathogen *Verticillium albo-atrum* R. and B. var. *menthae Nelson*, especially when compared with its *Mentha citrata* seed parent; its hardy characteristics under climatic conditions favorable to the growth of mint plants as represented by *Mentha piperita* L., especially in the Oregon area of mint production; and its production of an oil which has as its principal components linalyl acetate and linalool as compared with the oil of its male parent which has as its principal components menthone and pulegone.

No references cited.

ROBERT E. BAGWILL, Primary Examiner